United States Patent
Friebe et al.

(10) Patent No.: US 6,326,378 B1
(45) Date of Patent: Dec. 4, 2001

(54) USE OF THIADIAZOLO[4,3-A]PYRIDINE DERIVATIVES

(75) Inventors: Walter-Gunar Friebe, Mannheim; Wolfgang Schaumann, Heidelberg; Otto-Henning Wilhelms, Weinheim, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/622,325

(22) PCT Filed: Feb. 11, 1999

(86) PCT No.: PCT/EP99/00886

§ 371 Date: Oct. 5, 2000

§ 102(e) Date: Oct. 5, 2000

(87) PCT Pub. No.: WO99/42089

PCT Pub. Date: Aug. 26, 1999

(30) Foreign Application Priority Data

Feb. 17, 1998 (EP) .................................................. 98102675

(51) Int. Cl.$^7$ .................. A61K 31/437; A61K 31/4365; A61K 35/00
(52) U.S. Cl. .......................... 514/301; 514/293; 546/114; 546/83
(58) Field of Search ...................... 546/114, 83; 514/301, 514/293

(56) References Cited

U.S. PATENT DOCUMENTS 5,447,934 * 9/1995 Friebe .................................. 514/275

FOREIGN PATENT DOCUMENTS

WO 93/06109    4/1993 (WO) .

OTHER PUBLICATIONS

Nicholson CD et al., TIPS. 12, 19–27, Jan. 1991.*
Berkow, R. (Editor), "Merck Manual of Diagnosis and Therapy", Merck Research Laboratories, pp. 343–, paragraphs 5–7 (1992).
Potts et al., "Synthesis of Ring–Fused 1,2,4–Thiadiazoles" Synthesis, No. 12, pp. 1027–1029 (1986).

* cited by examiner

*Primary Examiner*—Evelyn Mei Huang
(74) *Attorney, Agent, or Firm*—George W. Johnston; Dennis P. Tramaloni; F. Aaron Dubberley

(57) ABSTRACT

The present invention relates to the method of treating leukemia, lymphoma or inhibiting the proliferation of cells with a compound of formula I.

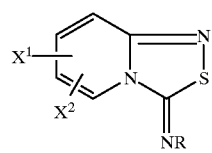

(I)

15 Claims, No Drawings

USE OF THIADIAZOLO[4,3-A]PYRIDINE DERIVATIVES

This application is the national phase of PCT/EP99/00886, filed Feb. 11, 1999.

The present invention relates to the use of thiadiazolo[4,3-a]pyridine derivatives for the production of medicaments for the treatment of diseases which are modulated by the inhibition of phosphodiesterase(s) (PDE). The invention relates in particular to the use of substances having a great therapeutic breadth with preferred inhibition of phosphodiesterases of types III and IV, preferably of type IV.

Previously disclosed PDE IV inhibitors caused unpleasant side effects in experimental animals and in man, such as production of, for example, nausea, giddiness and vomiting, as well as undesired cardiovascular effects such as lowering of blood pressure and tachycardia. However, compounds of the general formula I showed a great therapeutic breadth in in-vivo animal models. The side effects of previously known PDE IV inhibitors can thus be markedly decreased.

The compounds according to the invention are thiadiazolo[4,3-a]pyridine derivatives of the general formula I

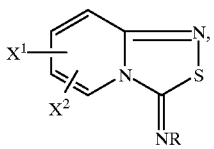

(I)

in which $X^1$ and $X^2$, identically or differently, are hydrogen, a $C_1$- to $C_6$-alkyl radical or a halogen atom or, if they are in adjacent positions, form a fused phenyl ring together with the carbon atoms carrying them, and R is a carbocyclic or heterocyclic saturated or unsaturated radical, which if desired can be mono- or polysubstituted by halogen, cyano, nitro, $C_1$- to $C_6$-alkyl, $C_1$- to $C_6$-haloalkyl, hydroxyl, $C_1$- to $C_6$-alkoxy, methylenedioxy, $C_1$- to $C_6$-alkylthio, $C_1$- to $C_6$-haloalkylthio, amino, $C_1$- to $C_6$-alkylamino, $C_2$- to $C_{12}$-dialkylamino, pyrrolyl, carboxyl, carbamoyl, benzyl $C_1$- to $C_6$-hydroxyalkyl, $C_2$- to $C_7$-carboxyalkyl, $C_2$- to $C_7$-alkoxycarbonyl-$C_1$- to $C_6$-alkyl, carbamoyl-$C_1$- to $C_6$-alkyl, N-hydroxy-N—$C_1$- to $C_6$-alkylcarbamoyl-$C_1$- to $C_6$-alkyl or $C_2$- to $C_6$-alkenyl, and their physiologically tolerable salts.

The alkyl radicals in the mentioned alkyl, alkoxy, alkylthio and (di)alkylamino groups and also the alkenyl radicals can be straight-chain or branched. Preferred alkyl radicals in these groups are the methyl, ethyl, n-propyl, isopropyl, n-butyl, isobutyl, tert-butyl, n-pentyl and 3-pentyl radical, preferred alkenyl radicals are the vinyl and the allyl radical.

A $C_1$–$C_6$-haloalkyl radical is preferably trifluoromethyl.

Possible halogen atoms are fluorine, chlorine and bromine.

Carbocyclic radicals are the phenyl, cyclohexyl and cyclopentyl radical. Possible heterocyclic radicals are pyridyl, piperidinyl, pyrimidinyl, pyrrolidinyl, isoxazolyl, oxazolyl, thiazolyl, thiazolinyl, triazolyl and tetrazolyl radicals.

Preferred compounds of the formula I are compounds in which $X^1$ is hydrogen, methyl or chlorine, $X^2$ is hydrogen or $X^1$ and $X^2$ together form a fused phenyl ring and R is a phenyl ring which can be mono- or disubstituted by fluorine, chlorine, methyl, methoxy, tert-butyl, isopropoxy, trifluoromethyl, trifluoromethylthio, hydroxyl, nitrile, nitro, hydroxymethyl, methylenedioxy, diethylamino, methylthio, pyrrolyl, methoxycarbonylmethyl, carboxymethyl, N-hydroxy-N-methylcarbamoylmethyl or N-tetrazolylcarbamoylmethyl, or is a thiazolyl, pyridinyl, tetrazolyl, pyrimidyl or cyclohexyl radical.

Apart from the compounds mentioned in the examples, the invention relates in particular to all substances which have any possible combination of the substituents mentioned in the examples.

The synthesis of some of the compounds is described in WO 93/06109. Alternatively, a compound of the general formula II

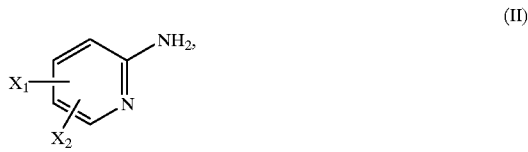

(II)

in which $X^1$ and $X^2$ have the abovementioned meaning, can be reacted in a known manner either a) with a compound of the formula III

ClSCCl₃ (III), or a reactive derivative thereof and a compound of the general formula IV

H₂N—R (IV), in which R has the abovementioned meaning, or b) with a compound of the general formula V

YS—CY=N—R (V), in which R has the abovementioned meaning and Y is a halogen atom, and then, if desired, a radical R can be converted into another radical given by the definition and the compound of the formula I obtained, if desired, can be converted into a salt by reaction with physiologically tolerable acids or bases.

Possible halogen atoms for Y are, in particular, chlorine and bromine.

The process is preferably carried out in such a way that a compound of the general formula II is first condensed with a compound of the formula III and the product obtained is isolated. This intermediate is then reacted with a compound of the general formula IV.

Another variant consists in allowing the reaction mixture obtained from the reaction of a compound of the formula II with a compound of the formula III to react with a compound of the formula IV without isolation of the intermediate.

The reactions are expediently carried out in a solvent such as water, ether, a lower alcohol such as, for example, methanol or ethanol or a halogenated hydrocarbon such as dichloromethane or trichloromethane with addition of a base such as triethylamine or sodium carbonate at temperatures between –20 and 50° C., preferably between 0° C. and room temperature.

The compounds of the formulae II, IV and V are known from the literature or can easily be prepared by trivial methods starting from known compounds.

Conversion of a radical R into another radical R is carried out, for example, by ether cleavage using a protic acid or Lewis acid such as hydrogen bromide, hydrogen chloride, hydrogen iodide, aluminium trichloride, boron trichloride or by alkylation of a hydroxyl group using the desired alkyl halide or alkyl sulphate.

A carboxyl group contained in R can be converted into an ester group or carboxamide function, if desired by means of a reactive derivative such as a halide, imidazolide or anhydride; an ester group contained in R can be converted into the carboxyl group by acidic or basic hydrolysis and into the carboxamide group by aminolysis.

Possible pharmacologically tolerable salts are, in particular, alkali metal, alkaline earth metal and ammonium salts and optionally salts with non-toxic inorganic or organic acids such as, for example, hydrochloric acid, sulphuric acid, phosphoric acid, hydrobromic acid, acetic acid, lactic acid, citric acid, malic acid, benzoic acid, salicylic acid, malonic acid, maleic acid, succinic acid or diaminocaproic acid.

The salts are obtained in a customary manner, e.g. by neutralization of the compounds of the formula I using the appropriate alkali solutions or acids.

It is described in WO 93/06109 that the compounds of the formula I inhibit the antigen-mediated contraction of lung tissue strips and prevent the lethality of an endotoxin shock.

PDE inhibitors intervene in the signal transduction cascade mediated by cyclic adenosine monophosphate (cAMP). PDE IV isoenzymes are found in various tissues and leukocyte types. They prevent the activation of leukocytes, thus also, inter alia, the secretion of TNF-α and can therefore also be used, for example, for treatment of cachexia.

The compounds of the formula I inhibit phosphodiesterase(s) (PDEs), preferably isoenzymes of the subclass type IV, with a simultaneous great therapeutic breadth. The compounds of the formula I are particularly suitable for medicaments for the preventive and/or symptomatic therapy of disorders whose causes lie in faulty regulation of intracellular signal transduction reactions which are controlled by cyclic nucleotides, in particular adenosine monophosphate (cAMP).

In particular, the compounds of formula I can be used for the production of medicaments for the treatment of disorders which are modulated by the inhibition of phosphodiesterase(s) (PDE) via cyclic nucleotides, especially cyclic adenosine monophosphate.

Examples of disorders which can be preventively or therapeutically treated by the compounds of the general formula I are: proliferatory disorders including tumours, lymphomas, leukaemias, atherosclerosis and glomerulopathies, furthermore disorders with reduction of learning ability and/or memory such as, for example, Alzheimer's syndrome, furthermore obesity, and also impotence and erectile insufficiency.

Surprisingly, it was possible to show that the compounds of the general formula I inhibit phosphodiesterase(s) (PDE), but preferably PDE of the subclass IV. Various isoenzymes of the phosphodiesterases are known (PDE I–PDE VII) PDE I, IV and V are found in mast cells, PDE III and IV in basophils, PDE IV in eosinophils, neutrophils and monocytes in each case, PDE II, III and IV in macrophages, PDE II–V and VII in T lymphocytes, PDE II, III and V in platelets, PDE II, IV and V in endothelial cells and PDE I–V in epithelial cells.

Compounds are preferred in which the quotient of the $IC_{50}$ values of isolated PDE IV to PDE III is at least 2, particularly preferably greater than 3. Preferentially, the $IC_{50}$ value for PDE IV is in the micromolar range, particularly preferably between 5 and 50 micromol.

The compounds of the general formula I exhibit a great therapeutic breadth in in-vivo animal models.

This is understood as meaning substances which have no disadvantageous side effects at a multiple of the therapeutically active plasma level in in-vivo tests. In the case of PDE III or IV inhibitors, side effects is understood as meaning a) lowering of the arterial blood pressure by more than 20%, b) raising of the heart rate by 20%, c) action on the CNS with production of stimulation, tremor, nausea and vomiting at oral doses which correspond to less than 2 times, preferably 5 times, the therapeutically necessary dose.

An example of a non-specific phosphodiesterase inhibitor employed for therapy and having a small therapeutic breadth is, for example, theophylline. Even at slightly increased doses, theophylline causes, inter alia, nausea, giddiness, tachycardia and tremor.

The compounds of the general formula I are suitable for the production of medicaments for the treatment of disorders which are modulated by inhibition of phosphodiesterases. Phosphodiesterase IV is preferably inhibited. Examples of disorders which can be preventively or therapeutically treated by the compounds of the general formula I are: proliferative disorders including tumours, lymphomas, leukaemias, atherosclerosis and glomerulopathies, memory and/or learning ability disorders (inter alia Alzheimer's), impotency due to erectile insufficiency and obesity, furthermore, for example, ischaemic or thrombolytic disorders, such as, for example, coronary infarct or cerebral infarct and additionally serum sickness.

For the production of medicaments, the compounds of the general formula I are mixed in a manner known per se with suitable pharmaceutical excipients, aromatizers, flavourings and colourants and shaped, for example, as tablets or coated tablets or suspended or dissolved in water or oil, such as, for example, olive oil, with addition of appropriate auxiliaries.

The substances of the general formula I can be administered orally and parenterally in liquid or solid form. The injection medium used is preferably water which contains the stabilizers, solubilizers and/or buffers customary in the case of injection solutions.

Additives of this type are, for example, tartrate or borate buffers, ethanol, dimethyl sulphoxide, complexing agents (such as ethylenediaminetetraacetic acid), high molecular weight polymers (such as liquid polyethylene oxide) for viscosity regulation or polyethylene derivatives of sorbitol anhydrides.

Solid excipients are, for example, starch, lactose, mannitol, methylcellulose, talc, highly disperse silicic acid, higher molecular weight polymers (such as polyethylene glycols).

If desired, preparations suitable for oral administration can contain flavourings and sweeteners. For external application, the substances I according to the invention can also be used in the form of powders, ointments and patches. To this end, they are mixed, for example, with powdered, physiologically tolerable diluents or customary ointment bases or attached to a patch base using customary technology.

The dose administered depends on the age, the health and the weight of the recipient, the extent of disease, the nature of simultaneous further treatments which are optionally carried out, the frequency of the treatment and the type of action desired. Customarily, the daily dose of the active compound is 0.1 to 50 mg/kg of body weight. Normally, 0.5 to 40 and preferably 1.0 to 20 mg/kg/day in one or more administrations per day are effective in order to obtain the desired results.

This dose can be given in the form of 1, 2 or more tablets daily. Alternatively, with suitable pharmaceutical technology, administration can be carried out every 2 days. The person skilled in the art can easily determine from the daily dose the appropriate active compound content of the tablets, depending on the administration scheme.

Apart from the substances mentioned in the examples, within the meaning of the present invention the use of the following compounds is preferred:
1. 4-(3H-[1,2,4]Thiadiazolo[4,3-a]pyridin-3-ylideneamino) phenylacetic acid N-(1H-tetrazol-5-yl)amide
2. 3-(2-Pyrimidinylimino)-3H-[1,2,4]thiadiazolo[4,3-a] pyridine
3. 5-Methyl-3-(4-pyridinylimino)-3H-[1,2,4]thiadiazolo[4,3-a]pyridine
4. 6-Methyl-3-(4-pyridinylimino)-3H-[1,2,4]thiadiazolo[4,3-a]pyridine
5. 8-Methyl-3-(4-pyridinylimino)-3H-[1,2,4]thiadiazolo[4,3-a]pyridine

EXAMPLE 1

3-(Thiazol-2-ylimino)-3H-[1,2,4]thiadiazolo[4,3-a]pyridine

A solution of 5.6 g (60 mmol) of 2-aminopyridine and 8.3 ml of triethylamine in 50 ml of chloroform is added dropwise at 0° C. to a solution of 6.6 ml (60 mmol) of trichloromethanesulphenyl chloride in 900 ml of chloroform. The mixture is stirred for 10 min and a solution of 6.0 g (60 mmol) of 2-aminothiazole and 25 ml of triethylamine in 100 ml of chloroform is added dropwise. After stirring at room temperature for 3 h, the mixture is concentrated and the precipitate is washed with methanol. 8.9 g of title compound (63% of theory) of m.p. 169–171° C. remain.

EXAMPLE 2

The following are obtained from trichloromethanesulphenyl chloride, 2-aminopyridine and the respective amine in a manner analogous to that described in Example 1:

| Designation | Yield % | Melting point ° C. (solvent) |
|---|---|---|
| a) 3-(2-Pyridinylimino)-3H-[1,2,4]thiadiazolo[4,3-a]pyridine from 2-aminopyridine | 80 | 159–161 (ether) |
| b) 3-(4-Pyridinylimino)-3H-[1,2,4]thiadiazolo[4,3-a]pyridine from 4-aminopyridine | 37 | 185–186 (ethanol) |
| c) 3-Phenylimino-3H-[1,2,4]thiadiazol[4,3-a]pyridine from aniline | 67 | 64–86 (propanol) |
| d) 3-(4-Chlorophenylimino)-3H-[1,2,4]thiadiazolo[4,3-a]pyridine from 4-chloroaniline | 64 | 129–130 (2-propanol) |
| e) 3-(4-Methoxyphenylimino)-3H-[1,2,4]thiadiazolo[4,3-a]pyridine from 4-methoxyaniline | 69 | 90–92 (2-propanol) |
| f) 3-(4-Cyanophenylimino)-3H-[1,2,4]thiadiazolo[4,3-a]pyridine from 4-aminobenzonitrile | 57 | 149–150 (2-propanol) |
| g) 3-(4-Nitrophenylimino)-3H-[1,2,4]thiadiazolo[4,3-a]pyridine from 4-nitroaniline | 63 | 198–199 (2-propanol) |
| h) 3-Cyclohexylimino-3H-[1,2,4]thiadiazolo[4,3-a]pyridine hydrochloride from cyclohexylamine | 28 | 194–196 (ethyl acetate) |
| i) 3-(5-1H-Tetrazolylimino)-3H-[1,2,4]thiadiazolo[4,3-a]pyridine from 5-amino-1H-tetrazole | 29 | 282–283 (water) |
| j) 3-(4-Fluorophenylamino)-3H-[1,2,4]thiadiazolo[4,3-a]pyridine from 4-fluoroaniline | 67 | 138–140 (2-propanol) |
| k) 3-(2,4-Dichlorophenylimino)-3H-[1,2,4]thiadiazolo[4,3-a]pyridine from 2,4-dichloroaniline | 51 | 130–132 (2-propanol) |
| l) 3-(4-Methylphenylimino)-3H-[1,2,4]thiadiazolo[4,3-a]pyridine from 4-methylaniline | 59 | 106–108 (2-propanol) |
| m) 3-(3-Trifluoromethylphenylimino)-3H-[1,2,4]thiadiazolo[4,3-a]pyridine from 3-trifluoromethylaniline | 34 | 48–49 (2-propanol) |
| n) 3-(2-Hydroxymethylphenylimino)-3H-[1,2,4]-thiadiazolo[4,3-a]pyridine from 2-aminobenzyl alcohol | 49 | 118–119 (2-propanol) |
| o) 3-(2-Hydroxyphenylimino)-3H-[1,2,4]-thiadiazolo[4,3-a]pyridine from 2-aminophenol | 21 | 130–132 (2-propanol) |
| p) 3-(4-Hydroxy-2-methylphenylimino)-3H-[1,2,4]thiadiazolo[4,3-a]-pyridine from 4-amino-3-methylphenol | 49 | 241–243 (2-propanol) |
| q) 3-(3,4-Methylenedioxyphenylimino)-3H-[1,2,4]thiadiazolo-[4,3-a]-pyridine from 3,4-methylenedioxyaniline | 49 | 141–143 (2-propanol) |
| r) 3-(3-Trifluoromethylthiophenylimino)-3H-[1,2,4]thiadiazolo-[4,3-a]pyridine from 3-trifluoromethylthioaniline | 70 | 86–88 (2-propanol) |
| s) 3-(4-Diethylaminophenylimino)-3H-[1,2,4]thiadiazolo[4,3-a]pyridine from N,N-diethyl-1,4-phenylenediamine | 54 | 96–97 (2-propanol) |
| t) 3-(5-Methylisoxazoi-3-ylimino)-3H-[1,2,4]thiadiazolo[4,3-a]pyridine from 3-amino-5-methylisoxazole | 36 | 170–172 (2-propanol) |
| u) 3-(4,5-Dihydrothiazol-2-ylimino)-3H-[1,2,4]thiadiazolo[4,3-a]-pyridine from 2-amino-2-thiazoline | 55 | 106–108 (2-propanol) |
| v) 3-(1-Benzylpiperidin-4-ylimino)-3H-[1,2,4]thiadiazolo[4,3-a]-pyridine from 4-amino-1-benzylpiperidine | 55 | 90–92 (2-propanol) |
| w) 3-(3-Pyridinylimino)-3H-[1,2,4]-thiadiazolo[4,3-a]pyridine from 3-aminopyridine | 67 | 133–134 (2-propanol) |
| x) 3-(4-t-Butylphenylimino)-3H-[1,2,4]thiadiazolo[4,3-a]pyridine from 4-t-butylaniline | 46 | 72–74 (isohexane) |
| y) 3-(4-Isopropoxyphenylimino)-3H-[1,2,4]thiadiazolo[4,3-a]pyridine from 4-isopropoxyaniline | 52 | 94–95 (ether) |
| z) 3-(4-Methylthiophenylimino)-3H-[1,2,4]thiadiazolo[4,3-a]pyridine from 4-methylmercaptoaniline | 76 | 111–112 (2-propanol) |
| aa) 3-(4-Pyrrolophenylimino)-3H-[1,2,4]thiadiazolo[4,3-a]pyridine from N-(4-aminophenyl)pyrrole | 68 | 167–168 (ethyl acetate) |

EXAMPLE 3

7-Methyl-3-(4-pyridinylimino)-3H-[1, 2, 4]thiadiazolo[4,3-a]pyridine

A solution of 3.2 g (30 mmol) of 2-amino-4-methylpyridine and 4.2 ml of triethylamine in 25 ml of dichloromethane is added dropwise at 0° C. to a solution of 3.3 ml (30 mmol) of trichloromethanesulphenyl chloride in 450 ml of dichloromethane, the mixture is stirred for 10 min and a solution of 2.8 g (30 mmol) of 4-aminopyridine and 12 ml of triethylamine in 100 ml of dichloromethane is added dropwise. After stirring at room temperature for 3 h, the mixture is poured into water and extracted with ethyl acetate, the extract is dried and concentrated, and the residue is chromatographed on silica gel (eluant ethyl acetate/isohexane 1:1). 1.2 g of title compound (17% of theory) of m.p. 144–145° C. are isolated.

EXAMPLE 4

6-Chloro-3-(4-pyridinylimino)-3H-[1,2, 4]-thiadiazolo[4,3-a]pyridine

In an analogous manner to that described in Example 3, the title compound of m.p. 205–207° C. is obtained in 20% yield from 2-amino-5-chloropyridine and 4-aminopyridine.

EXAMPLE 5

3-Phenylimino-3H-[1,2,4]-thiadiazolo[4,3-a]quinoline

A solution of 4.1 g (21 mmol) of 1-chloro-1-phenyliminomethanesulphenyl chloride in 20 ml of dichloromethane is added dropwise at 0° C. to a solution of 3.1 g (21 mmol) of 2-aminoquinoline and 6 ml of triethylamine in 70 ml of dichloromethane, the mixture is stirred for 3 h at room temperature, the organic phase is washed with water, dried and concentrated, and the residue is chromatographed on silica gel. Using isohexane/ethyl acetate 9:1, 2.3 g of title compound (39% of theory) of m.p 116–118° C. are eluted.

EXAMPLE 6

3-(4-Pyridinylimino)-3H-[1,2,4]-thiadiazolo[4,3-a]quinoline

In an analogous manner to that described in Example 3, the title compound of m.p. 180–182° C. is obtained in 11% yield from 2-aminoquinoline and 4-aminopyridine.

EXAMPLE 7

3-(4-Methoxycarbonylmethylphenylimino)-3H-[1,2, 4]thiadiazolo[4,3-a]pyridine

In an analogous manner to that described in Example 1, the title compound of m.p. 151–152° C. (from ethyl acetate) is obtained in 41% yield from 2-aminopyridine and methyl 4-aminophenylacetate.

EXAMPLE 8

4-(3H-[1,2,4]Thiadiazolo[4,3-a]pyridin-3-ylidenamino)phenylacetic acid hydrochloride A mixture of 9.0 g (30 mmol) of the compound of Example 7, 100 ml of ethanol and 300 ml of N hydrochloric acid is stirred at 50° C. for 6 h. The mixture is concentrated and the residue is triturated with acetone. 8.9 g of title compound (92% of theory) of m.p. 209–211° C. remain.

EXAMPLE 9

4-(3H-[1,2,4]Thiadiazolo[4,3-a]-pyridin-3-ylidenamino)phenylacetic acid N-methylhydroxamide A solution of 1.7 ml of oxalyl chloride in 15 ml of dichloromethane is added dropwise at 0° C. to a mixture of 4.8 g (15 mmol) of the compound of Example 8, 90 ml of dichloromethane and 1 ml of dimethylformamide. The solution obtained is stirred for 40 min and then added dropwise to a solution of 5.0 g of N-methylhydroxylamine in 15 ml of triethylamine, 10 ml of water and 60 ml of tetrahydrofuran. After stirring for 30 min, the mixture is treated with 20 ml of water and extracted with dichloromethane, the extract is dried and concentrated, and the residue is purified on silica gel (eluent trichloroethane/methanol 95:5). 3.4 g of title compound (78% of theory) are isolated, which after trituration with ether melt at 135–136° C.

Pharmacological Investigations

EXAMPLE 10

The $IC_{50}$ values of the compound from Example 2b were determined to be $2 \times 10^{-5}$ mol/l (PDE IV) and $8 \times 10^{-5}$ mol/l (PDE III) on isolated human enzyme preparations.

EXAMPLE 11

Anti-proliferatory Action in Vitro

The compound from Example 2b inhibits the activation of various types of leucocytes under different stimuli. Cell types, parameters in order to determine the activation and $IC_{50}$ values (mg/l) are summarized in Table 1

TABLE 1

| Cell type | Stimulus | Parameter:Inhibition v. | $IC_{50}$ |
|---|---|---|---|
| Peripheral leucocytes | LPS | Secretion of TNFα | <3 |
| Lymphocytes | ConA | Thymidine incorporation | 2.8 |
| Lymphocytes | Mixed lymphocytes reaction | Thymidine incorporation | 7.6 |
| T Lymphoblasts | — | Thymidine incorporation | 6.4 |
| Basophilic granulocytes | Anti-IgE antibody | Proteinase release | 10 |
| Phagocytes (PMNs) | Zymosan | Chemiluminescence | 27 |

EXAMPLE 12

Toxicity and Therapeutic Breadth

The compound from Example 2b is well tolerated by small experimental animals (mice, rats, guinea pigs p.o. and i.p.) and by dogs p.o. It was not possible to determine any side effects (behaviour, body weight, histology, haematological and clinicochemical parameters) in rats after 2 weeks (40 mg/kg daily). In conscious dogs (beagles), the heart rate and the arterial blood pressure on administration of 24 mg/kg of the compound from Example 2b remained constant in the observation period up to 6 h after administration Ad (see Table 2). The behaviour of the dogs was normal. The emetic action typical of PDE IV inhibitors as a sign of CNS effects was not detectable. It was moreover found that triglycerides and GPT (the latter as a sign of liver damage) and blood glucose remained unchanged in the observation period.

TABLE 2

Effect on heart rate and on arterial blood pressure
of conscious dogs after oral administration of 24 mg/kg of the compound of Example 2b
Average values n = 5/group

| Admin. | MP | Preliminary value | Measurement . . . min after substance administration | | | | | | | | | |
|---|---|---|---|---|---|---|---|---|---|---|---|---|
| | | | 30 | 60 | 90 | 120 | 150 | 180 | 210 | 240 | 300 | 360 |
| 1 ml/kg Methyl cellulose 1% + 2% DMSO | HR | 83 | 85 | 79 | 83 | 80 | 81 | 76 | 84 | 74 | 77 | 75 |
| | SBP | 172 | 179 | 178 | 172 | 173 | 175 | 178 | 169 | 167 | 169 | 170 |
| | DBP | 70 | 65 | 66 | 63 | 64 | 64 | 65 | 63 | 62 | 62 | 65 |
| | MAP | 114 | 114 | 114 | 110 | 111 | 112 | 114 | 109 | 108 | 108 | 110 |
| 1 ml/kg Edible oil +2% DMSO | HR | 79 | 117 | 82 | 86 | 82 | 82 | 87 | 86 | 93 | 92 | 91 |
| | SBP | 171 | 181 | 178 | 173 | 175 | 179 | 179 | 174 | 169 | 169 | 174 |
| | DBP | 66 | 63 | 57 | 58 | 60 | 63 | 66 | 68 | 64 | 65 | 70 |
| | MAP | 111 | 113 | 109 | 107 | 109 | 113 | 114 | 114 | 109 | 110 | 115 |

Doses of this type caused average plasma levels of the active substances over several hours after administration which (markedly) exceed the necessary in vitro concentrations for significant inhibition of isolated humane PDE N or for inhibition of secretion of, for example TNF alpha (in each case $2 \times 10^{-5}$ mol/l).

What is claimed is:

1. A method of treating leukemia comprising:
administering to a recipient diagnosed with leukemia a therapeutically effective amount of a compound of formula I

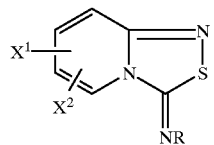

in which
$X^1$ and $X^2$, individually are hydrogen, a $C_1$- to $C_6$-alkyl radical or a halogen atom or, if they are in adjacent positions, form a fused phenyl ring together with the carbon atoms carrying them, and
R is a carbocyclic or heterocyclic saturated or unsaturated radical, optionally mono- or polysubstituted by halogen, cyano, nitro, $C_1$- to $C_6$-alkyl, $C_1$- to $C_6$-haloalkyl, hydroxyl, $C_1$- to $C_6$-alkoxy, methylenedioxy, $C_1$- to $C_6$-alkylthio, $C_1$- to $C_6$-haloalkylthio, amino, $C_1$- to $C_6$-alkylamino, $C_2$- to $C_{12}$-dialkylamino, pyrrolyl, carboxyl, carbamoyl, benzyl, $C_1$- to $C_6$-hydroxyalkyl, $C_2$- to $C_7$-carboxyalkyl, $C_2$- to $C_7$-alkoxycarbonyl-$C_1$- to $C_6$-alkyl, carbamoyl-$C_1$- to $C_6$-alkyl, N-hydroxy-N—$C_1$- to $C_6$-alkylcarbamoyl-$C_1$- to $C_6$-alkyl or $C_2$- to $C_6$-alkenyl,
or a physiologically tolerable salt of a compound of formula I.

2. The method of claim 1, wherein the therapeutically effective amount is from 0.1 mg of the compound of formula I per kilogram of the recipient per day to 50 mg of the compound of formula I per kilogram of the recipient per day.

3. The method according to claim 2, wherein
$X^1$ is hydrogen, methyl or chlorine,
$X^2$ is hydrogen; or $X^1$ and $X^2$ together form a fused phenyl ring, and
R is a phenyl ring optionally mono- or disubstituted by fluorine, chlorine, methyl, methoxy, tert.butyl, isopropoxy, trifluoromethyl, trifluoromethylthio, hydroxyl, nitrile, nitro, hydroxymethyl, methylenedioxy, diethylamino, methylthio, pyrrolyl, methoxycarbonylmethyl, carboxymethyl, N-hydroxy-N-methyl-carbamoylmethyl or N-tetrazolyl-carbamoylmethyl, or is a thiazolyl, pyridinyl, tetrazolyl, pyrimidyl or cyclohexyl radical.

4. The method according to claim 3, wherein the compound of formula I is selected from the group consisting of:
3-(thiazol-2-yl-imino)-3H-[1,2,4]-thiadiazolo[4,3-a]pyridine,
3-(2-pyridinyl-imino)-3H-[1,2,4]-thiadiazolo[4,3-a]pyridine,
3-(4-pyridinyl-imino)-3H-[1,2,4]-thiadiazolo[4,3-a]pyridine,
3-phenylimino-3H-[2,4]-thiadiazol[4,3-a]pyridine,
3-(4-chloro-phenylimino)-3H-[1,2,4]-thiadiazolo[4,3-a]pyridine,
3-(4-methoxy-phenylimino)-3H-[1,2,4]-thiadiazolo[4,3-a]pyridine,
3-(4-cyano-phenylimino)-3H-[1,2,4]-thiadiazolo[4,3-a]pyridine,
3-(4-nitro-phenylimino)-3H-[1,2,4]-thiadiazolo[4,3-a]pyridine,
3-cyclohexylimino-3H-[1,2,4]-thiadiazolo[4,3-a]pyridine-hydrochloroid,
3-(5-1H-tetrazolyl-imino)-3H-[1,2,4]-thiadiazolo[4,3-a]pyridine,
3-(4-fluoro-phenylamino)-3H-[1,2,4]-thiadiazolo[4,3-a]pyridine,
3-(2,4-dichloro-phenylimino)-3H-[1,2,4]-thiadiazolo[4,3-a]pyridine,
3-(4-methyl-phenylimino)-3H-[1,2,4]-thiadiazolo[4,3-a]pyridine,
3-(3-trifluoromethyl-phenylimino)-3H-[1,2,4]-thiadiazolo[4,3-a]pyridine,
3-(2-hydroxymethyl-phenylimino)-3H-[1,2,4]-thiadiazolo[4,3-a]pyridine,
3-(2-hydroxy-phenylimino)-3H-[1,2,4]-thiadiazolo[4,3-a]pyridine,
3-(4-hydroxy-2-methyl-phenylimino)-3H-[1,2,4]-thiadiazolo[4,3-a]pyridine,
3-(3,4-methylenedioxy-phenylimino)-3H-[1,2,4]-thiadiazolo[4,3-a]pyridine, 3-(3-trifluoromethylthio-phenylimino)-3H-[1,2,4]-thiadiazolo[4,3-a]pyridine,
3-(4-diethylamino-phenylimino)-3H-[1,2,4]-thiadiazolo[4,3-a]pyridine,
3-(5-methyl-isoxazol-3-ylimino)-3H-[1,2,4]-thiadiazolo[4,3-a]pyridine,
3-(4,5-dihydro-thiazole-2-ylimino)-3H-[1,2,4]-thiadiazolo[4,3-a]pyridine,
3-(1-benzyl-piperidin-4-ylimino)-3H-[1,2,4]-thiadiazolo[4,3-a]pyridine,
3-(3-pyridinyl-imino)-3H-[1,2,4]-thiadiazolo[4,3-a]pyridine,
3-(4-t-butyl-phenylimino)-3H-[1,2,4]-thiadiazolo[4,3-a]pyridine,
3-(4-isopropoxy-phenylimino)-3H-[1,2,4]-thiadiazolo[4,3-a]pyridine,
3-(4-methylthio-phenylimino)-3H-[1,2,4]-thiadiazolo[4,3-a]pyridine,
3-(4-pyrrolo-phenylimino)-3H-[1,2,4]-thiadiazolo[4,3-a]pyridine,
7-methyl-3-(4-pyridinyl-imino)-3H-[1,2,4]-thiadiazolo[4,3-a]pyridine,
6-chloro-3-(4-pyridinyl-imino)-3H-[1,2,4]-thiadiazolo[4,3-a]pyridine,
3-phenylimino-3H-[1,2,4]-thiadiazolo[4,3-a]quinoline,
3-(4-pyridinyl-imino)-3H-[1,2,4]-thiadiazolo[4,3-a]quinoline,
3-(4-methoxycarbonylmethyl-phenylimino)-3H-[1,2,4]-thiadiazolo[4,3-a]pyridine,
4-(3H-[1,2,4]-thiadiazolo[4,3-a]pyridin-3-ylideneamino)-phenylacetic acid hydrochloride and
4-(3H-[1,2,4]-thiadiazolo[4,3-a]pyridine-3-ylideneamino)-phenylacetic acid N-methyl-hydroxamide.

5. The method of claim 4, wherein the therapeutically effective amount is from 0.5 mg of the compound of formula I per kilogram of the recipient per day to 40 mg of the compound of formula I per kilogram of the recipient per day.

6. The method of claim 5, wherein the therapeutically effective amount is from 1.0 mg of the compound of formula I per kilogram of the recipient per day to 20 mg of the compound of formula I per kilogram of the recipient per day.

7. A method of treating lymphoma comprising:
administering to a recipient diagnosed with lymphoma a therapeutically effective amount of a compound of formula I

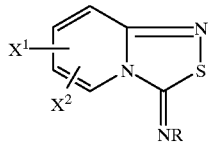

in which
$X^1$ and $X^2$, individually are hydrogen, a $C_1$- to $C_6$-alkyl radical or a halogen atom or, if they are in adjacent positions, form a fused phenyl ring together with the carbon atoms carrying them, and
R is a carbocyclic or heterocyclic saturated or unsaturated radical, optionally mono- or polysubstituted by halogen, cyano, nitro, $C_1$- to $C_6$-alkyl, $C_1$- to $C_6$-haloalkyl, hydroxyl, $C_1$- to $C_6$-alkoxy, methylenedioxy, $C_1$- to $C_6$-alkylthio, $C_1$- to $C_6$-haloalkylthio, amino, $C_1$- to $C_6$-alkylamino, $C_2$- to $C_{12}$-dialkylamino, pyrrolyl, carboxyl, carbamoyl, benzyl, $C_1$- to $C_6$-hydroxyalkyl, $C_2$- to $C_7$-carboxyalkyl, $C_2$- to $C_7$-alkoxycarbonyl-$C_1$- to $C_6$-alkyl, carbamoyl-$C_1$- to $C_6$-alkyl, N-hydroxy-N—$C_1$- to $C_6$-alkylcarbamoyl-$C_1$- to $C_6$-alkyl or $C_2$- to $C_6$-alkenyl,
or a physiologically tolerable salt of a compound of formula I.

8. The method of claim 7, wherein the therapeutically effective amount is from 0.1 mg of the compound of formula I per kilogram of the recipient per day to 50 mg of the compound of formula I per kilogram of the recipient per day.

9. The method of claim 8, wherein
$X^1$ is hydrogen, methyl or chlorine,
$X^2$ is hydrogen; or
$X^1$ and $X^2$ together form a fused phenyl ring, and
R is a phenyl ring optionally mono- or disubstituted by fluorine, chlorine, methyl, methoxy, tert.butyl, isopropoxy, trifluoromethyl, trifluoromethylthio, hydroxyl, nitrile, nitro, hydroxymethyl, methylenedioxy, diethylamino, methylthio, pyrrolyl, methoxycarbonylmethyl, carboxymethyl,N-hydroxy-N-methyl-carbamoylmethyl or N-tetrazolyl-carbamoylmethyl, or is a thiazolyl, pyridinyl, tetrazolyl, pyrimidyl or cyclohexyl radical.

10. The method of claim 9, wherein the compound of formula I is selected from the group consisting of:
3-(thiazol-2-yl-imino)-3H-[1,2,4]-thiadiazolo[4,3-a]pyridine,
3-(2-pyridinyl-imino)-3H-[1,2,4]-thiadiazolo[4,3-a]pyridine,
3-(4-pyridinyl-imino)-3H-[1,2,4]-thiadiazolo[4,3-a]pyridine,
3-phenylimino-3H-[1,2,4]-thiadiazol[4,3-a]pyridine,
3-(4-chloro-phenylimino)-3H-[1,2,4]-thiadiazolo[4,3-a]pyridine,
3-(4-methoxy-phenylimino)-3H-[1,2,4]-thiadiazolo[4,3-a]pyridine,
3-(4-cyano-phenylimino)-3H-[1,2,4]-thiadiazolo[4,3-a]pyridine,
3-(4-nitro-phenylimino)-3H-[1,2,4]-thiadiazolo[4,3-a]pyridine,
3-cyclohexylimino-3H-[1,2,4]-thiadiazolo[4,3-a]pyridine-hydrochloroid,
3-(5-1H-tetrazolyl-imino)-3H-[1,2,4]-thiadiazolo[4,3-a]pyridine,
3-(4-fluoro-phenylamino)-3H-[1,2,4]-thiadiazolo[4,3-a]pyridine,
3-(2,4-dichloro-phenylimino)-3H-[1,2,4]-thiadiazolo[4,3-a]pyridine,
3-(4-methyl-phenylimino)-3H-[1,2,4]-thiadiazolo[4,3-a]pyridine,
3-(3-trifluoromethyl-phenylimino)-3H-[1,2,4]-thiadiazolo[4,3-a]pyridine,
3-(2-hydroxymethyl-phenylimino)-3H-[1,2,4]-thiadiazolo[4,3-a]pyridine,
3-(2-hydroxy-phenylimino)-3H-[1,2,4]-thiadiazolo[4,3-a]pyridine,
3-(4-hydroxy-2-methyl-phenylimino)-3H-[1,2,4]-thiadiazolo[4,3-a]pyridine,
3-(3,4-methylenedioxy-phenylimino)-3H-[1,2,4]-thiadiazolo[4,3-a]pyridine,
3-(3-trifluoromethylthio-phenylimino)-3H-[1,2,4]-thiadiazolo[4,3-a]pyridine,
3-(4-diethylamino-phenylimino)-3H-[1,2,4]-thiadiazolo[4,3-a]pyridine,
3-(5-methyl-isoxazol-3-ylimino)-3H-[1,2,4]-thiadiazolo[4,3-a]pyridine,
3-(4,5-dihydro-thiazole-2-ylimino)-3H-[1,2,4]-thiadiazolo[4,3-a]pyridine, 3-(1-benzyl-piperidin-4-ylimino)-3H-[1,2,4]-thiadiazolo[4,3-a]pyridine,
3-(3-pyridinyl-imino)-3H-[1,2,4]-thiadiazolo[4,3-a]pyridine,
3-(4-t-butyl-phenylimino)-3H-[1,2,4]-thiadiazolo[4,3-a]pyridine,
3-(4-isopropoxy-phenylimino)-3H-[1,2,4]-thiadiazolo[4,3-a]pyridine,
3-(4-methylthio-phenylimino)-3H-[1,2,4]-thiadiazolo[4,3-a]pyridine,
3-(4-pyrrolo-phenylimino)-3H-[1,2,4]-thiadiazolo[4,3-a]pyridine,
7-methyl-3-(4-pyridinyl-imino)-3H-[1,2,4]-thiadiazolo[4,3-a]pyridine,
6-chloro-3-(4-pyridinyl-imino)-3H-[1,2,4]-thiadiazolo[4,3-a]pyridine,
3-phenylimino-3H-[1,2,4]-thiadiazolo[4,3-a]quinoline,
3-(4-pyridinyl-imino)-3H-[1,2,4]-thiadiazolo[4,3-a]quinoline,
3-(4-methoxycarbonylmethyl-phenylimino)-3H-[1,2,4]-thiadiazolo[4,3-a]pyridine,
4-(3H-[1,2,4]-thiadiazolo[4,3-a]pyridin-3-ylideneamino)-phenylacetic acid hydrochloride and
4-(3H-[1,2,4]-thiadiazolo[4,3-a]pyridine-3-ylideneamino)-phenylacetic acid N-methyl-hydroxamide.

11. The method of claim 10, wherein the therapeutically effective amount is from 0.5 mg of the compound of formula I per kilogram of the recipient per day to 40 mg of the compound of formula I per kilogram of the recipient per day.

12. The method of claim 11, wherein the therapeutically effective amount is from 1.0 mg of the compound of formula I per kilogram of the recipient per day to 20 mg of the compound of formula I per kilogram of the recipient per day.

13. A method of inhibiting proliferating cells selected from a group consisting of leukocytes, lymphocytes, T lymphoblasts, basophilic granulocytes and phagocytes comprising:
administering to said cells a proliferation inhibiting amount of a compound of formula I

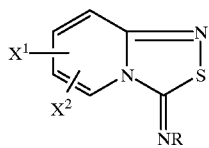

(I)

in which
$X^1$ and $X^2$, individually are hydrogen, a $C_1$- to $C_6$-alkyl radical or a halogen atom or, if they are in adjacent positions, form a fused phenyl ring together with the carbon atoms carrying them, and
R is a carbocyclic or heterocyclic saturated or unsaturated radical, optionally mono- or polysubstituted by halogen, cyano, nitro, $C_1$- to $C_6$-alkyl, $C_1$- to $C_6$-haloalkyl, hydroxyl, $C_1$- to $C_6$-alkoxy, methylenedioxy, $C_1$- to $C_6$-alkylthio, $C_1$- to $C_6$-haloalkylthio, amino, $C_1$- to $C_6$-alkylamino, $C_2$- to $C_{12}$-dialkylamino, pyrrolyl, carboxyl, carbamoyl, benzyl, $C_1$- to $C_6$-hydroxyalkyl, $C_2$- to $C_7$-carboxyalkyl, $C_2$- to $C_7$-alkoxycarbonyl-$C_1$- to $C_6$-alkyl, carbamoyl-$C_1$- to $C_6$-alkyl, N-hydroxy-N—$C_1$- to $C_6$-alkylcarbamoyl-$C_1$- to $C_6$-alkyl or $C_2$- to $C_6$-alkenyl,
or a physiologically tolerable salt of a compound of formula I.

14. The method of claim 13, wherein
$X^1$ is hydrogen, methyl or chlorine,
$X^2$ is hydrogen; or
$X^1$ and $X^2$ together form a fused phenyl ring, and
R is a phenyl ring optionally mono- or disubstituted by fluorine, chlorine, methyl, methoxy, tert.butyl, isopropoxy, trifluoromethyl, trifluoromethylthio, hydroxyl, nitrile, nitro, hydroxymethyl, methylenedioxy, diethylamino, methylthio, pyrrolyl, methoxycarbonylmethyl, carboxymethyl, N-hydroxy-N-methyl-carbamoylmethyl or N-tetrazolyl-carbamoylmethyl, or is a thiazolyl, pyridinyl, tetrazolyl, pyrimidyl or cyclohexyl radical.

15. The method of claim 14, wherein the compound of formula I is selected from the group consisting of:
3-(thiazol-2-yl-imino)-3H-[1,2,4]-thiadiazolo[4,3-a]pyridine,
3-(2-pyridinyl-imino)-3H-[1,2,4]-thiadiazolo[4,3-a]pyridine,
3-(4-pyridinyl-imino)-3H-[1,2,4]-thiadiazolo[4,3-a]pyridine,
3-phenylimino-3H-[1,2,4]-thiadiazol[4,3-a]pyridine,
3-(4-chloro-phenylimino)-3H-[1,2,4]-thiadiazolo[4,3-a]pyridine,
3-(4-methoxy-phenylimino)-3H-[1,2,4]-thiadiazolo[4,3-a]pyridine,
3-(4-cyano-phenylimino)-3H-[1,2,4]-thiadiazolo[4,3-a]pyridine,
3-(4-nitro-phenylimino)-3H-[1,2,4]-thiadiazolo[4,3-a]pyridine,
3-cyclohexylimino-3H-[1,2,4]-thiadiazolo[4,3-a]pyridine-hydrochloroid,
3-(5-1H-tetrazolyl-imino)-3H-[1,2,4]-thiadiazolo[4,3-a]pyridine,
3-(4-fluoro-phenylamino)-3H-[1,2,4]-thiadiazolo[4,3-a]pyridine,
3-(2,4-dichloro-phenylimino)-3H-[1,2,4]-thiadiazolo[4,3-a]pyridine,
3-(4-methyl-phenylimino)-3H-[1,2,4]-thiadiazolo[4,3-a]pyridine,
3-(3-trifluoromethyl-phenylimino)-3H-[1,2,4]-thiadiazolo[4,3-a]pyridine,
3-(2-hydroxymethyl-phenylimino)-3H-[1,2,4]-thiadiazolo[4,3-a]pyridine,
3-(2-hydroxy-phenylimino)-3H-[1,2,4]-thiadiazolo[4,3-a]pyridine,
3-(4-hydroxy-2-methyl-phenylimino)-3H-[1,2,4]-thiadiazolo[4,3-a]pyridine,
3-(3,4-methylenedioxy-phenylimino)-3H-[1,2,4]-thiadiazolo[4,3-a]pyridine,
3-(3-trifluoromethylthio-phenylimino)-3H-[1,2,4]-thiadiazolo[4,3-a]pyridine,
3-(4-diethylamino-phenylimino)-3H-[1,2,4]-thiadiazolo[4,3-a]pyridine,
3-(5-methyl-isoxazol-3-ylimino)-3H-[1,2,4]-thiadiazolo[4,3-a]pyridine,
3-(4,5-dihydro-thiazole-2-ylimino)-3H-[1,2,4]-thiadiazolo[4,3-a]pyridine,
3-(1-benzyl-piperidin-4-ylimino)-3H-[1,2,4]-thiadiazolo[4,3-a]pyridine,
3-(3-pyridinyl-imino)-3H-[1,2,4]-thiadiazolo[4,3-a]pyridine,
3-(4-t-butyl-phenylimino)-3H-[1,2,4]-thiadiazolo[4,3-a]pyridine,
3-(4-isopropoxy-phenylimino)-3H-[1,2,4]-thiadiazolo[4,3-a]pyridine,
3-(4-methylthio-phenylimino)-3H-[1,2,4]-thiadiazolo[4,3-a]pyridine, 3-(4-pyrrolo-phenylimino)-3H-[1,2,4]-thiadiazolo[4,3-a]pyridine, 7-methyl-3-(4-pyridinyl-imino)-3H-[1,2,4]-thiadiazolo[4,3-a]pyridine, 6-chloro-3-(4-pyridinyl-imino)-3H-[1,2,4]-thiadiazolo[4,3-a]pyridine, 3-phenylimino-3H-[1,2,4]-thiadiazolo[4,3-a]quinoline, 3-(4-pyridinyl-imino)-3H-[1,2,4]-thiadiazolo[4,3-a]quinoline, 3-(4-methoxycarbonylmethyl-phenylimino)-3H-[1,2,4]-thiadiazolo[4,3-a]pyridine, 4-(3H-[1,2,4]-thiadiazolo[4,3-a]pyridin-3-ylideneamino)-phenylacetic acid hydrochloride and 4-(3H-[1,2,4]-thiadiazolo[4,3-a]pyridine-3-ylideneamino)-phenylacetic acid N-methyl-hydroxamide.

* * * * *